United States Patent [19]

Terry

[11] Patent Number: 5,229,299
[45] Date of Patent: Jul. 20, 1993

[54] TEST DEVICES AND METHODS FOR DETERMINING HALIDES IN AQUEOUS SAMPLES

[75] Inventor: Carol Ann Terry, Cassopolis, Mich.

[73] Assignee: Environmental Test Systems, Inc., Elkhart, Ind.

[21] Appl. No.: 872,268

[22] Filed: Apr. 21, 1992

[51] Int. Cl.$^5$ .............. G01N 33/38; G01N 33/52
[52] U.S. Cl. .................... 436/125; 436/124; 436/166; 436/169; 422/56
[58] Field of Search .............. 422/56–58, 422/61; 436/166, 124, 125, 73, 169; 264/40.1

[56] References Cited

U.S. PATENT DOCUMENTS 4,444,193  4/1984  Fogt et al. ...................... 422/58
4,650,768  3/1987  Cahill et al. ..................... 422/58

Primary Examiner—Lyle Alexander
Attorney, Agent, or Firm—Harry T. Stephenson

[57] ABSTRACT

A test device and method of use for determination of aqueous halide ions is described. The device has a porous matrix containing a silver dichromate reagent that gives a colorimetric response in the presence of halide ions and a cationic substance that prevents the formation of silver oxide products. The cationic substance has no colorimetric response in the presence of halide ions that would interfere with the measurement of the colorimetric change of the silver dichromate reagent.

12 Claims, 1 Drawing Sheet

TEST DEVICES AND METHODS FOR DETERMINING HALIDES IN AQUEOUS SAMPLES

FIELD OF THE INVENTION

The present invention relates to improved solid state test devices and methods for determining the presence and amount of halide ion in complex test fluids using a silver dichromate reagent system. More specifically, it relates to means for reducing or eliminating the effect of interfering substances when a solid state silver dichromate test system is used to determine halides, such as chloride ion, in highly alkaline fluids such as wet concrete.

BACKGROUND OF THE INVENTION

The science of analytical chemistry and particularly simple to use solid state test devices using analytical chemistry principles has made dramatic progress over the past decade or so. At one time such devices simply gave an indication of the presence of a substance or a gross condition of the fluid being analyzed, such as, for example, the use of litmus paper to determine if the fluid was acidic or basic. Now such devices can give answers which are as precise, specific and sensitive as those obtained using laboratory procedures and conditions. Moreover, such devices can quite often be used without accompanying instrumentation which permits their use in the field or "on-site" to give instant answers. This obviously eliminates the need for preserving sample integrity, simplifies record keeping and allows the user to take rapid corrective measures.

Present simple to use solid state testing devices usually take the form of either (1) a paper matrix pad impregnated with a reagent which develops a color when the entire pad is immersed in or contacted with an analyte in solution or (2) a reagent impregnated bibulous or porous matrix which is enclosed in a fluid impervious sheath or covering which restricts the flow of fluid being tested to a defined opening, usually an end portion of the sheath. In use, this latter type device is contacted with the fluid being tested such that the opening is exposed to the fluid which wicks up or into the bibulous matrix by capillary action (or is pulled or pushed into and through the porous matrix using applied force such as pressure or vacuum), wherein an analyte or a conversion product thereof in the fluid reacts with the reagent in the matrix to form a localized reaction product giving a visual response as the fluid moves through the matrix.

The pad type reagent strip device is usually made quantitative or semi-quantitative by using a chromogen in the reacting mixture which responds proportionally to the amount of analyte in the fluid being tested. This response can either be read visually by comparison to a developed color chart or by inserting the pad in a reflectance photometer which electronically "reads" the amount of color formed and interprets this as a quantitative value. The photometer obviously gives the analysis a higher degree of precision and sensitivity.

The sheath enclosed reagent incorporated matrix (SERIM) type device is interpreted by measuring the reaction of the analyte with the reagent as the fluid moves through the matrix. This is accomplished by effecting a localized visual change in the matrix by such reaction until the analyte is exhausted from the moving front of the wicking fluid. The sheath enclosing the matrix usually contains a means such as spaced marking lines and a numerical scale for measuring the extent of the chemical reaction. The number opposite the visual change is then compared to a calibration chart to give a quantitative result; however, if the device can be fabricated consistently, the numbers on the device can be the actual values for the concentration of analyte in the fluid being tested.

It has long been known that silver dichromate reagent systems incorporated in a porous matrix are excellent devices to test for the presence of halides such as chloride ion in a wide variety of Health related and commercially important substances such as body fluids, foods and beverages, industrial processing fluids and building supplies. Basically the devices are contacted with the fluid being tested and any color change in the reddish brown color of the test reagent matrix is used to judge the presence and amount of halide present in the fluid. It has, however, recently been found that complex alkaline fluids such as wet concrete or mortar contain interfering substances which react with the reagent system and cause a darkening effect in the matrix, thus preventing the facile reading of the color change. It has been particularly determined that alkaline fluids containing relatively high concentrations of hydroxyl ions suffer from the disadvantage that such hydroxyl ions react with the silver dichromate to form browninsh-black silver hydroxides which ultimately form black oxides and consequently prevent or obscure the detection and measurement of any white silver halide which causes the change in color in the silver dichromate reagent system.

DESCRIPTION OF THE PRIOR ART

The following patents and literature references give a background for the devices and methods associated with the present invention. There is no known prior art directly relating to this invention.

The basic construction of silver dichromate matrix impregnated test paper is described by Hoffman, I. et al., "New Rapid Paper Strip Method for Determining Urine Chloride", New York State Journal of Medicine, issued Aug. 1, 1964, pages 1988 and 1989.

U.S. Pat. No. 3,447,904 discloses a basic test strip device containing a complex silver or mercury salt and a chromogen reagent system for detecting chlorides in test fluids.

U.S. Pat. No. 3,620,677 discloses a basic SERIM type device which involves incorporating various reagents in a porous matrix and enclosing the matrix in a fluid impervious sheath. Such devices are manufactured by Environmental Test Systems, Inc. of Elkhart, Ind. U.S.A. and sold under the registered tradename QUANTAB.

U.S. Patent No. 3,811,840 discloses a test device wherein the fluid being analyzed is forced to flow through an aperture in a matrix having a reagent immobilized therein, this first matrix being backed up with a second matrix to force additional fluid through the aperture. All reactions involved in these pad type devices are of the colorimetric or color producing variety and are read in the aperture or device opening.

U.S. Pat. No. 4,650,768 describes a hybrid test strip/SERIM device for detecting chlorides in which a fluid impervious coating is applied to the top surface of the matrix of a reagent strip device such that when the strip is contacted with the fluid being tested, the fluid is forced to enter the sides of the matrix. A distinctive reaction pattern is generated in the matrix depending on the concentration of chloride in the fluid being tested.

SUMMARY OF THE INVENTION

The present invention relates to a means for eliminating or reducing the effect of interfering substances on the readability or measurement of the color change associated with the reaction of halides with silver dichromate reagent systems. Basically this means comprises the use of one or more interference reducing substances in combination with the reagent system to form a unitized test device or to pretreat the sample with such substances such that the color change associated with contact of the silver dichromate with the halide can be detected and measured.

DESCRIPTION OF THE PREFERRED EMBODIMENTS

Figure 1:
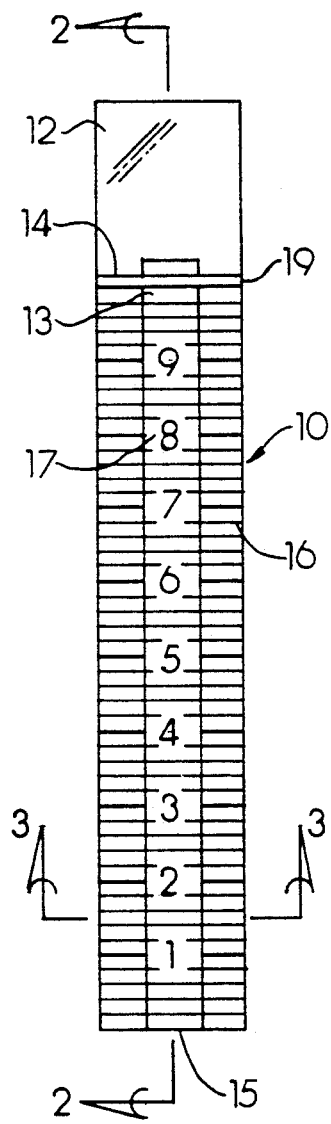
FIG. 1 is a front view of a device of the present invention wherein an elongated, flat porous matrix is contained in a continuous sheath open at both ends.

As used herein, the following definitions apply: analyte is defined as the chemical substance being detected; test reagent is defined as the silver dichromate component which react with the analyte (halide) to give a visually perceptible response thereto; test fluid is defined as the liquid environment which contains the analyte; matrix is defined as the inert bibulous or porous support for the test reagent; sheath is a test fluid impervious, transparent or translucent (light transmissive) material which intimately covers and encloses the matrix; color change means an actual change in the color of the reagent system upon contact with the analyte or if the test fluid is allowed to wick through the matrix, the degree of color change along the length of the matrix; matrix localized reaction product means that the visually perceptible substance formed by the reaction of the analyte with the test reagent is retained at the site in the matrix where the reaction takes place; reagent strip device means a test device which utilizes a matrix containing the dried solids of a reagent system which when rehydrated with the test fluid reacts with the analyte to give a detectable color response thereto; SERIM is an acronym for sheath enclosed reagent incorporated matrix type devices as disclosed herein; and basic SERIM device refers to a test means which comprises a matrix and primary reagent contained in a sheath having controlled openings to permit the test fluid to enter.

The interference reducing substances of the present invention basically comprise a class of compounds consisting of water soluble cationic substances, the anionic portion of which does no interfere with the silver dichromate test reagent. More particularly, such compounds may be any non-halogenated cationic compound, preferably polyvalent, which forms hydroxides which are less soluble that silver hydroxide in the fluid being tested. Cationic substances such as zinc, magnesium, lead, aluminum, manganese, copper, tin, cerium, bismuth, lanthanum and iron$^{++}$ and salts thereof such as acetates, nitrates, and sulfates are particularly useful and may be utilized in the present invention. Those cationic substances which form white or non-chromogenic hydroxides are of particular importance in the present invention since they may be advantageously used by incorporation directly into a matrix type device. Zinc acetate has been shown to be a preferable interference reducing substance for use in the compositions and devices of the present invention.

The cationic interference reducing substance of the present invention may be used either singly or in combination. The required concentration of such materials usually depends upon the mode of use and the alkalinity of the substance being tested. Basically, the amount used is that necessary to prevent or substantially reduce the blackening without affecting the performance of the color reaction or the flow of fluids in or through the test device. The effective amount used can range from about 20 mM to 200 mM with the preferable amount ranging about from 50 mM to 100 mM.

Various methods may be used to prepare the silver dichromate reagent systems. A preferable method is to use a double impregnation technique. Basically, a length of halide free filter paper is first run through a 0.8% solution of silver nitrate, dried and then run through a 0.4% to 0.8% solution of potassium dichromate and again dried. The resultant reagent paper has a reddish brown coloration and when contacted with halide ion turns bright white. This is caused by reaction of the halide ion with the silver dichromate to form an insoluble white silver halide precipitate.

A preferred test device format of the present invention is s SERIM type device which comprises the use of flat, paper or paper-like matrices encased or laminated between sheets of plastic film. The matrices are usually elongated strips of paper impregnated with silver dichromate reagent. The end portions of the plastic film are cut off exposing the matrix to the prevailing environment. The lower openend is contacted with the fluid being tested and the upper end permits air to escape from the device.

Another SERIM type test device structure comprises the use of cylindrical, filter tip type matrices in which the reagents are contained in the filter tip material and the sheath is a continuous tube of material which surrounds the matrices. The resulting cylindrical devices are used in the same manner as the flat devices but have the advantage of increased volume and are more amenable to pulling the fluid through the column by means of a negative pressure exerted on the upper opening.

A third test device structure which can be used with the present test composition comprises a reagent strip like structure wherein the matrix is attached to a plastic strip which forms a handle for the device and the surface of the matrix is covered with a fluid impervious film. Any fluid contacting the device must enter the side edges of the matrix and wick toward the center. The result is that a "X" pattern is formed on the surface of the matrix, the positioning of the "X" on the matrix depending on the concentration of halide in the fluid being tested.

Finally, a standard reagent strip test device may be utilized which is simply dipped into the fluid being tested and the color response to halide measured by reference to a color chart. The color chart is usually calibrated to give concentration of halide in the fluid being tested.

Figure 2:
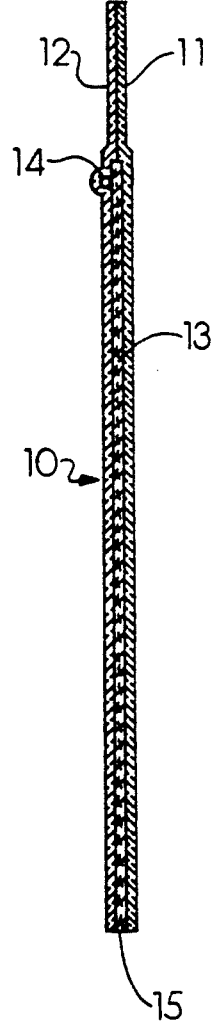
FIG. 2 is a longitudinal sectional view of the device of FIG. 1 taken along the line 2—2.

Referring now to the drawings, FIGS. 1 and 2 show a front view and a side sectional view respectively of a SERIM device 10 wherein a strip of reagent impregnated paper 13 forming a matrix is laminated between two sheets of transparent plastic 11 and 12, the face portion of the front sheet 12 being printed with marking lines 16 and a numerical scale 17 for ease of reading the extent of reaction. The upper end of the matrix 13 is covered with a signal string 14 which is likewise laminated between plastic sheets 11 and 12 but exposed to the atmosphere at opening 19. An opening 15 is positioned at the lower end of device allowing fluid to enter matrix 13. The front sheet 12 must be light transmissive; however, the rear sheet 11 may be opaque to enhance the reading of the extent of the reaction in the matrix 13.

Figure 3:
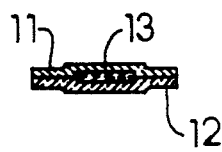
FIG. 3 is latitudinal sectional view of the device of FIG. 1 taken along the line 3—3.

FIG. 3 is a cross sectional view of device 10 at line 3—3 showing matrix 13 laminated between plastic sheets 11 and 12.

Figure 4:
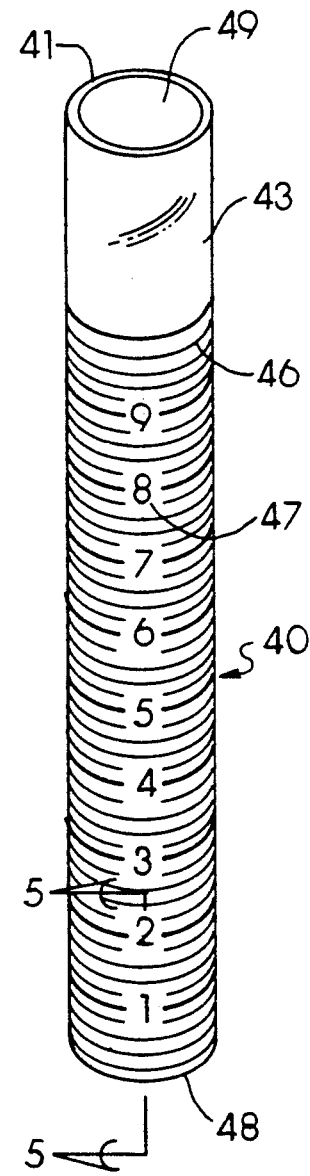
FIG. 4 is a perspective front view of a cylindrical device wherein the porous matrix is contained in a tube-shaped sheath.

FIG. 4 shows a perspective front view of a cylindrical, filter-tip type SERIM device 40, wherein the matrix 43 is encased in tubular plastic film sheath 41 which contains spaced marking lines of which 46 is representative and a numerical indication of line placement of which 47 is representative. The end portions of the device 40 are open at the upper end 49 and the lower end 48. In use the lower end opening 48 is placed in sufficient fluid to fill the device but not to the extent that it can enter the upper end opening 49.

Figure 5:
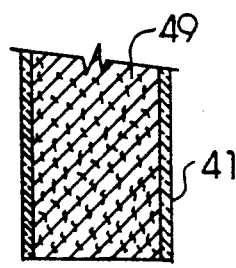
FIG. 5 is a longitudinal sectional view of the device shown in FIG. 4 taken along the line 5—5.

FIG. 5 is a cross sectional view of the lower end of device 40 taken along line 5—5.

Basic SERIM type devices using flat paper type matrices are fabricated as follows: 1. porous or bibulous paper is impregnated or incorporated with a reagent which reacts specifically with the analyte being detected to give a visual response; 2. the paper is dried, if necessary, and cut into elongated strips, the length and width depending on the wicking action desired; 3. the strips are then "laminated" between sheets of transparent plastic material such that the plastic material is in intimate contact with the reagent paper and the edge portions of the plastic surrounding the reagent are sealed; and, 4. the end portions are then opened to expose the paper. In use, one end portion of the resulting SERIM device is immersed into the fluid being tested which fluid moves through the matrix of the device. The analyte reacts with the reagent in the matrix until the analyte is exhausted, at which location on the matrix the reaction ceases. The fluid minus analyte continues through the matrix until reaching the top at which time the degree of reaction is "read". The extent of the reaction along the matrix is then measured and compared to a calibration chart to give a quantitative result.

Basic cylindrical type SERIM devices are fabricated as follows: 1. continuous filament material such as cellulose acetate or polyester is woven and shaped into cylindrical rods; 2. this porous material is impregnated with reagents and dried; 3. the impregnated rods are then encased into tightly fitting transparent plastic sheaths and cut to length; and, 4. the plastic sheaths are either initially provided with or are later printed with graduated markings.

Reagent strip devices are prepared by impregnating the matrix which usually comprises absorbent paper with the necessary reagents and attaching a small segment of such paper to a plastic handle to provide for ease of use of the paper. Obviously automated methods of manufacturing such test devices may be used in commercial operations. In use the paper matrix holding the reagent is simple dipped into the fluid being tested, withdrawn and the color compared to a color chart or read with a photometer.

The raw materials used in constructing the devices of the present invention are many and diverse; however, basically the matrix materials must be porous to the fluids being tested and when constructing a SERIM device the sheath or laminating materials must be impervious to such fluids in order to direct its flow into and through the device. Moreover, the matrix must be inert to both the reagents and the analyte. It must, however, be capable of containing the reagents and, if necessary, holding the reagent in place when the device is immersed into the test fluid or while the test fluid flows through the matrix. Common matrix substances are cellulosic materials such as filter paper, glass fibers, porous polymer materials and combinations of such materials. Some examples of such materials include cellulose or derivatives of cellulose such as a wide array of substituted ion-exchange celluloses, continuous filament synthetic cellulose acetate or polyester filter materials, ion exchange resin loaded materials, and, in addition, a wide range of adsorbants such as silica gel, activated alumina, diatomaceous earth, silicas and derivatives thereof, and activated carbon. Common sheath materials include Mylar film, polyethylene, polypropylene, polyesters, and other transparent or translucent (light transmissive) film forming or heat shrinkable materials. The choice of sheath material is dependent on the type of device, the fluid being tested and the lamination or encasement process.

A particularly advantageous application of the present invention can be found in the testing of concrete for chloride ion or salt. As previously noted, the common SERIM device for chloride testing utilizes a matrix impregnated with silver dichromate which when contacted with chloride ion forms an insoluble white silver chloride precipitate. Accordingly, the length of white precipitate formed in the matrix or column is proportional to the amount of chloride ion present in the test fluid. However, when this device is used to test wet mortar or concrete, which is an extremely complex mixture of materials and highly alkaline, the fluid entering the device causes a brownish-black precipitate or coloration to form which obscures the visualization at lower concentration levels of the white silver chloride precipitate, making the test unreliable at such concentration levels. This problem can be alleviated or obviated by using the interference reducing substances of the present invention in conjunction with the SERIM device either as an integral part of the reagent composition itself or as a pretreatment section which the fluid contacts before it enters the reagent impregnated wick. When using the cationic substance as a pretreatment of the fluid entering the SERIM device, it may be incorporated into a porous matrix and that matrix connected to or laid over the lower end (or the entire length) of the wick and the pretreatment area and the wick enclosed in the sheath. Obviously, many variations of the use of the cationic substances described herein may be employed without deviating from the spirit and scope of the present invention.

The following Examples are illustrative of the present invention.

EXAMPLES

Note: In Examples 1 and 6-14 which follow, commercially available SERIM devices, i.e. QUANTAB chloride titrators, Product No. 1175, Control Code 0023086 were used. This product is basically strips of paper impregnated with silver dichromate which are laminated between two thin sheets of plastic film, the top film being transparent and containing marking or calibration lines to measure the extent of reaction of the chlorideto the dichromate reagent in the paper. The devices are open at the bottom and have a signal string laminated between the films in contact with the top ofthe impregnated paper. The signal string is impregnated with a dyestuff responsive to an aqueous fluid which serves to mark the end of the test procedure as well as providing a vent for the wicking mechanism.

In Examples 2-5 in which SERIM devices were used in conjunction with the cationic substances recited, reagent paper was prepared using the materials and reagent concentrations previously noted and laminated between sheets of polyester, polyethylene film.

EXAMPLE 1

Test for Chloride in Mortar Using Standard SERIM Devices

The lower ends of three SERIM standard test devices were immersed about two cm into fresh mortar having a sodium chloride concentration of about 100 ppm. Fluid from the mortar wicked up the device in about 6-7 minutes. The extent of reaction in the reagent matrix was obscured by the formation of a brownish-black coloration making the test devices unusable.

EXAMPLES 2-4

In the following examples, the indicated materials were used in SERIM devices to test for chloride in the mortar described in Example 1. The blackening coloration observed in Example 1 was substantially reduced in all cases.

| Example | Cation (salt) | Concentration |
| --- | --- | --- |
| 2 | Zinc Acetate | 0.1 M |
| 3 | Aluminum Nitrate | 1.0 M |
| 4 | Magnesium Nitrate | 2.0 M |

EXAMPLES 5-14

In the following examples, the cation listed was added to the mortar recited in Example 1 in the concentration of 0.1 gm per 100 gm mortar and standard SERIM test devices utilized. In all cases the blackening effect of the mortar was substantially reduced and the test device could be easily read.

| Example | Cation (salt) |
| --- | --- |
| 5 | Cerium Nitrate |
| 6 | Zinc Acetate |
| 7 | Magnesium Acetate |
| 8 | Lead Acetate |
| 9 | Aluminum Sulfate |
| 10 | Aluminum Nitrate |
| 11 | Magnesium Sulfate |
| 12 | Magnesium Nitrate |
| 13 | Copper Sulfate |
| 14 | Bismuth Nitrate |

What is claimed is:

1. A device for testing fluids containing alkaline hydroxyl ions for the presence and amount of halide ions using a porous matrix incorporating an effective amount of a silver dichromate reagent which gives a measurable colorimetric response in the presence of halide ions, the improvement comprising including in the matrix an effective amount of a cationic substance that substantially prevents the formation of silver hydroxide and other oxide products, where the substance has no colorimetric response in the presence of halide ions that would interfere with the measurement of the colorimetric change in the silver dichromate reagent system.

2. A device as in claim 1 wherein the cationic substance is selected from the group consisting of non halogen water soluble salts of zinc, aluminum, magnesium, lead, bismuth, iron $++$ and molybdenum.

3. A device as in claim 1 wherein the matrix is a flat, paper material.

4. A device as in claim 1 wherein the matrix and sheath are cylindrically shaped.

5. A device as in claim 1 wherein the fluid being tested is wet mortar.

6. A device as in claim 1 wherein the porous matrix is contained in a light transmissive, fluid impervious covering material having controlled openings to allow the test fluid to enter by capillary action with the silver dichromate reagent system.

7. A device as in claim 6 wherein the covering material is an elongated sheath having the controlled opening at a first end and an opening at the opposite second end to allow the test fluid to enter at the first end and flow through the matrix to the second end.

8. A device as in claim 6 wherein the cationic substance is zinc acetate.

9. A method for testing fluid from wet mortar for the presence and amount of chloride ion using an effective amount of a silver dichromate reagent system which gives a measurable colorimetric response in the presence of halide ions, the improvement comprising including in the reagent an effective amount of a cationic substance that substantially prevents the formation of silver hydroxide and other oxide products, where the substance has no colorimetric response in the presence of halide ions that would interfere with the measurement of the colorimetric change in the silver dichromate reagent system.

10. A method as in claim 9 wherein the cationic substance is included with the silver dichromate to form a unitized reagent system and the reagent system is contacted with the fluid from the wet mortar.

11. A method as in claim 9 wherein the cationic substance is selected from the group consisting of water soluble non halogenated salts of zinc, aluminum, magnesium, lead, manganese, cerium, copper, bismuth, iron and molybdenum.

12. A method as in claim 11 wherein the cationic substance is zinc acetate.

* * * * *